United States Patent
Kusuoka et al.

(10) Patent No.: US 8,765,640 B2
(45) Date of Patent: Jul. 1, 2014

(54) CRYSTAL FORMS OF SULFONYLUREA COMPOUND AND METHOD FOR PRODUCING THE SAME

(75) Inventors: Yoshiyuki Kusuoka, Funabashi (JP); Yoshihiko Nakaya, Funabashi (JP); Nao Kitayado, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 180 days.

(21) Appl. No.: 13/505,185

(22) PCT Filed: Oct. 25, 2010

(86) PCT No.: PCT/JP2010/068845
§ 371 (c)(1),
(2), (4) Date: Apr. 30, 2012

(87) PCT Pub. No.: WO2011/055649
PCT Pub. Date: May 12, 2011

(65) Prior Publication Data
US 2012/0220461 A1  Aug. 30, 2012

(30) Foreign Application Priority Data

Nov. 4, 2009  (JP) ................................. 2009-252981
Aug. 27, 2010  (JP) ................................. 2010-190267

(51) Int. Cl.
C07D 413/14 (2006.01)
A01N 43/88 (2006.01)

(52) U.S. Cl.
USPC ............................................. 504/223; 544/65

(58) Field of Classification Search
CPC ............................. C07D 413/14; A01N 43/88
USPC ............................................. 544/65; 504/223
See application file for complete search history.

(56) References Cited

U.S. PATENT DOCUMENTS

| | | |
|---|---|---|
| 5,527,911 A | 6/1996 | Guglielmetti et al. |
| 5,631,720 A | 5/1997 | Guglielmetti et al. |
| 5,754,271 A | 5/1998 | Guglielmetti et al. |
| 2008/0064600 A1 | 3/2008 | Kita et al. |
| 2009/0137819 A1 | 5/2009 | Yasuoka et al. |
| 2010/0016584 A1 | 1/2010 | Kita et al. |

FOREIGN PATENT DOCUMENTS

| | | |
|---|---|---|
| JP | A-6-135967 | 5/1994 |
| JP | A-2001-2677 | 1/2001 |
| JP | A-2002-293791 | 10/2002 |
| JP | A-2007-332129 | 12/2007 |
| WO | WO 03/014732 A1 | 2/2003 |
| WO | WO 2005/103044 A1 | 11/2005 |
| WO | WO 2005103044 A1 * | 11/2005 |
| WO | WO 2007046440 A1 * | 4/2007 |

OTHER PUBLICATIONS

*Journal of Japanese Association of Crystal Growth*, vol. 13, No. 1, p. 100, 1986 (with abstract).
*Bunri Gijutsu*, vol. 25, No. 5, pp. 9(381)-14(386), 38(410), 1995 (with abstract).
Nov. 16, 2010 Written Opinion of the International Searching Authority issued in International Patent Application No. PCT/JP2010/068845 (with translation).
Nov. 16, 2010 International Search Report issued in International Patent Application No. PCT/JP2010/068845 (with translation).
Oct. 15, 2013 Office Action issued in Columbian Patent Application No. 12-093-450 (with partial translation).
Morissette et al., "High-throughput crystallization: polymorphs, salts, co-crystals and solvates of pharmaceutical solids," Advanced Drug Delivery Reviews 56 (2004), pp. 275-300.
Vippagunta et al., "Crystalline Solids," Advanced Drug Delivery Reviews 48 (2001) pp. 3-26.
Preformulación: Polimorfismo: Formación de Sales, 2 Farmacia Práctica Remington 2226-2231 (19$^{th}$ ed. 1995).

* cited by examiner

*Primary Examiner* — Kahsay Habte
(74) *Attorney, Agent, or Firm* — Oliff PLC

(57) ABSTRACT

Crystal forms of sulfonylurea compound and method for producing the same. It has been found that a sulfonylurea compound of Formula (1):

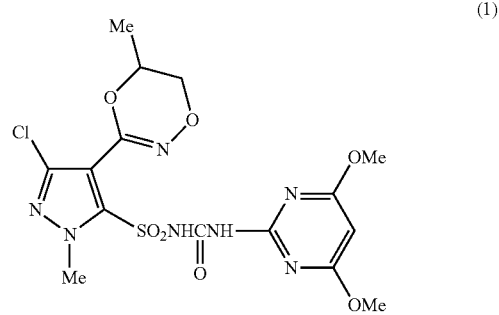

has two types of crystal polymorphisms and four types of pseudo crystal polymorphisms. A production method of each crystal form of the sulfonylurea compound of Formula (1) through recrystallization or solvate has been also found. In addition, a suspension of a composition containing the crystal that is improved in storage stability is provided.

8 Claims, 7 Drawing Sheets

CRYSTAL FORMS OF SULFONYLUREA COMPOUND AND METHOD FOR PRODUCING THE SAME

TECHNICAL FIELD

The present invention relates to crystal forms that a sulfonylurea compound of Formula (1) below, which is a compound having herbicidal activity useful as a herbicide, can take, a method for producing the same, and a suspension of a composition containing the crystal forms.

BACKGROUND ART

Sulfonylurea compound of Formula (1) below has been known (for example, Patent Document 1). Their crystal forms and methods for producing the same, however, remain unknown.

RELATED-ART DOCUMENTS

Patent Documents

Patent Document 1: International Publication No. WO 2005/103044 pamphlet

SUMMARY OF THE INVENTION

Problem to be Solved by the Invention

It is an object of the present invention to provide a novel crystal of a sulfonylurea compound of Formula (1) below and a method for producing the same. It is another object of the present invention to provide a suspension of a composition containing the crystal and having improved storage stability.

Means for Solving the Problem

As a result of assiduous research in view of the foregoing, the inventors of the present invention have found that a sulfonylurea compound of Formula (1) below has two types of crystal polymorphisms and four types of pseudo crystal polymorphisms and have developed a method for producing the same. Specifically, the present invention provides:

[1] A sulfonylurea compound of a crystal form A having characteristic peaks at 2θ=7.12°, 8.16°, 8.88°, 9.60°, 12.48°, 13.24°, 16.88°, 17.80°, 18.56°, 19.32°, 20.2°, 21.04°, 22.56°, 23.28°, 24.24°, 24.68°, 27.52°, 31.28° in powder X-ray diffraction by a Cu—Kα ray among crystal forms that a sulfonylurea compound of Formula (1):

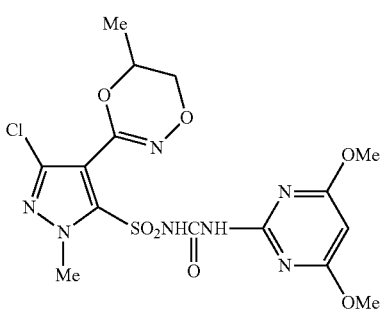

is capable of taking.

[2] A sulfonylurea compound of a crystal form B having peaks at 2θ=7.72°, 8.20°, 9.80°, 10.24°, 14.64°, 15.36°, 16.44°, 20.12°, 21.08°, 21.52°, 23.32°, 24.32°, 28.88°, and 31.28° in powder X-ray diffraction by a Cu—Kα ray among crystal forms that a sulfonylurea compound of Formula (1) is capable of taking.

[3] A sulfonylurea compound of a crystal form C having peaks at 2θ=6.24°, 9.24°, 11.56°, 12.44°, 13.16°, 14.16°, 14.80°, 15.92°, 16.52°, 17.72°, 18.56°, 18.96°, 19.88°, 21.36°, 22.12°, 23.28°, 24.40°, 24.92°, 25.84°, 27.40°, 28.00°, 28.48°, 31.24°, and 31.88° in powder X-ray diffraction by a Cu—Kα ray among crystal forms that a sulfonylurea compound of Formula (1) is capable of taking.

[4] A sulfonylurea compound of a crystal form D having peaks at 2θ=14.43°, 11.52°, 12.28°, 14.04°, 14.64°, 16.12°, 17.52°, 18.8°, 19.84°, 21.16°, 23.00°, 24.72°, 25.64°, 26.08°, 27.24°, 27.84°, 28.32°, 31.04°, and 31.76° in powder X-ray diffraction in the powder X-ray diffraction by a Cu—Kα, ray among crystal forms that a sulfonylurea compound of Formula (1) is capable of taking.

[5] A sulfonylurea compound of a crystal form E having peaks at 2θ=7.64°, 8.12°, 8.84°, 9.80°, 10.16°, 12.44°, 13.96°, 14.52°, 15.24°, 16.36°, 16.84°, 17.72°, 18.24°, 18.76°, 19.32°, 20.00°, 21.00°, 21.44°, 22.48°, 23.24°, 24.2°, 25.04°, 25.56°, 27.84°, 28.8°, 31.2°, 33.12°, and 34.12° in powder X-ray diffraction by a Cu—Kα ray among crystal forms that a sulfonylurea compound of Formula (1) is capable of taking.

[6] A sulfonylurea compound of a crystal form F having peaks at 2θ=7.00°, 7.48°, 8.16°, 8.84°, 9.56°, 11.44°, 12.00°, 12.48°, 13.04°, 13.52°, 14.04°, 15.08°, 15.68°, 16.36°, 16.88°, 17.88°, 18.36°, 19.88°, 20.36°, 21.2°, 22.00°, 22.80, 23.48°, 24.20°, 25.28°, 26.56°, 27.84°, 29.32°, 29.80°, 30.48°, 32.12°, and 34.12° in powder X-ray diffraction by a Cu—Kα ray among crystal forms that a sulfonylurea compound of Formula (1) is capable of taking.

[7] A production method of a crystal containing, as a main component, the crystal form A described in [1], the production method including: dissolving a sulfonylurea compound of Formula (1) in a solvent mixture of o-xylene and heptane; and cooling down the resultant solution, evaporating the solvent from the solution, or adding a poor solvent to the solution to elevate the degree of supersaturation of the solution to precipitate a crystal.

[8] A production method of a crystal containing, as a main component, the crystal form B described in [2], the production method including removing volatile components from the sulfonylurea compound of the crystal form C described in [3] under a heating condition.

[9] A production method of a crystal containing, as a main component, the crystal form C described in [3], the production method including: dissolving a sulfonylurea compound of Formula (1) in chlorobenzene; and cooling down the resultant solution, evaporating the solvent from the solution, or adding a poor solvent to the solution to elevate the degree of supersaturation of the solution to precipitate a crystal.

[10] A production method of a crystal containing, as a main component, the crystal form D described in [4], the production method including: dissolving a sulfonylurea compound of Formula (1) in bromobenzene; and cooling down the resultant solution, evaporating the solvent from the solution, or adding a poor solvent to the solution to elevate the degree of supersaturation of the solution to precipitate a crystal.

[11] A production method of a crystal containing, as a main component, the crystal form E described in [5], the production method including: dissolving a sulfonylurea compound of Formula (1) in toluene; and cooling down the resultant solution, evaporating the solvent from the solution, or adding a poor solvent to the solution to elevate the degree of supersaturation of the solution to precipitate a crystal.

[12] A production method of a crystal containing, as a main component, the crystal form F described in [6], the production method including: dissolving a sulfonylurea compound of Formula (1) in 1,2-dichloroethane; and cooling down the resultant solution or evaporating the solvent from the solution to elevate the degree of supersaturation of the solution to precipitate a crystal.

[13] A production method of a crystal containing, as a main component, the crystal form A described in [1], the production method including heating the sulfonylurea compound of the crystal form C described in [3] to remove volatile components therefrom.

[14] A production method of a crystal containing, as a main component, the crystal form A described in [1], the production method including heating the sulfonylurea compound of the crystal form D described in [4] to remove volatile components therefrom.

[15] A production method of a crystal containing, as a main component, the crystal form A described in [1], the production method including heating the sulfonylurea compound of the crystal form E described in [5] to remove volatile components therefrom.

[16] A production method of a crystal containing, as a main component, the crystal form A described in [1], the production method including heating the sulfonylurea compound of the crystal form F described in [6] to remove volatile components therefrom.

[17] A suspension of a composition containing the sulfonylurea compound of the crystal form A described in [1] and a dispersion medium.

[18] The suspension of a composition according to [17] further containing a surfactant, in which the dispersion medium is water.

[19] The suspension of a composition according to [17] including a sulfonylurea compound of Formula (1) containing a crystal that is in the crystal form A in a content of 10 to 100% by weight.

[20] The suspension of a composition according to [18] including a sulfonylurea compound of Formula (1) containing a crystal that is in the crystal form A in a content of 10 to 100% by weight.

[21] The suspension of a composition according to [17] including a sulfonylurea compound of Formula (1) containing a crystal that is in the crystal form A in a content of 50 to 100% by weight.

[22] The suspension of a composition according to [18] including a sulfonylurea compound of Formula (1) containing a crystal that is in the crystal form A in a content of 50 to 100% by weight.

Effects of the Invention

According to the present invention, various crystal forms of a sulfonylurea compound of Formula (1) can be obtained with advantageous reproducibility. A suspension of a composition containing the crystal form A of a sulfonylurea compound of Formula (1) suppresses aging decomposition of the sulfonylurea compound of Formula (1), so that the composition has good storage stability.

MODES FOR CARRYING OUT THE INVENTION

In the present invention, for the discrimination of the crystal form, a powder X-ray diffraction measurement, a differential thermal analysis, $^{13}$C CP/TOSS NMR, a Raman spectroscopy, and the like are effective, however, the method for the discrimination is not limited to these measurement methods.

The sulfonylurea compound of Formula (1) is produced, for example, by the method shown in Reaction Formula 1 below.

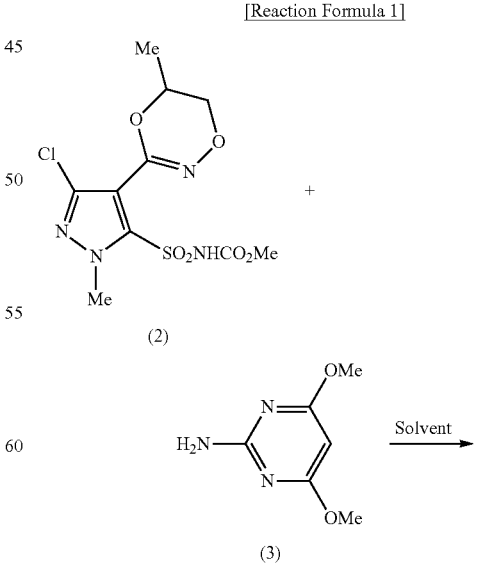

[Reaction Formula 1]

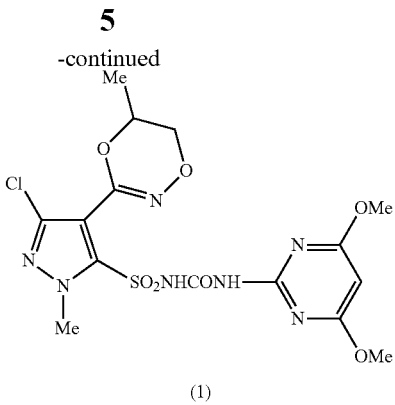

(1)

That is, by heating a sulfonyl carbamate compound (2) and an aminopyrimidine compound (3) in an organic solvent to remove the generated methanol from the reaction system, the sulfonylurea compound (1) can be produced.

The sulfonylurea compound of the crystal form A has a melting point of 187 to 188° C., and in the differential thermal analysis thereof, there are not observed an endothermic peak and a loss of the sample weight in a range of temperatures lower than the melting point thereof. The sulfonylurea compound of the crystal form A has characteristic peaks at 2θ=7.12°, 8.16°, 8.88°, 9.60°, 12.48°, 13.24°, 16.88°, 17.80°, 18.56°, 19.32°, 20.2°, 21.04°, 22.56°, 23.28°, 24.24°, 24.68°, 27.52°, 31.28° in the powder X-ray diffraction, and has characteristic peaks at 17.55 ppm, 18.95 ppm, 40.44 ppm, 41.23 ppm, 53.87 ppm, 54.72 ppm, 55.81 ppm, 66.06 ppm, 68.18 ppm, 69.41 ppm, 73.04 ppm, 86.39 ppm, 90.14 ppm, 113.51 ppm, 114.64 ppm, 136.99 ppm, 138.31 ppm, 149.31 ppm, 150.66 ppm, 155.21 ppm, 156.32 ppm, 169.48 ppm, 170.31 ppm, 172.10 ppm, 17105 ppm in $^{13}$C CP/TOSS NMR. The change thereof by heating or friction is not observed.

The sulfonylurea compound of the crystal form B has a melting point of 176 to 177° C., and by drying a sulfonylurea compound of the crystal form C produced at −15° C. or less, a sulfonylurea compound of a pure crystal form B can be obtained. In the differential thermal analysis thereof, there are not observed an endothermic peak and a loss of the sample weight in a range of temperatures lower than the melting point thereof. The sulfonylurea compound of the crystal form B has characteristic peaks at 2θ=7.72°, 8.20°, 9.80°, 10.24°, 14.64°, 15.36°, 16.44°, 20.12°, 21.08°, 21.52°, 23.32°, 24.32°, 28.88°, 31.28° in the powder X-ray diffraction, and has characteristic peaks at 16.16 ppm, 17.17 ppm, 42.53 ppm, 43.05 ppm, 54.14 ppm, 55.77 ppm, 68.59 ppm, 72.19 ppm, 85.98 ppm, 115.15 ppm, 115.74 ppm, 137.49 ppm, 139.51 ppm, 148.95 ppm, 150.12 ppm, 156.00 ppm, 170.66 ppm, 173.04 ppm in $^{13}$C CP/TOSS NMR measurement. Although a change thereof by heating is not observed, by suspending the sulfonylurea compound of the crystal form B in a solvent and stirring the resultant suspension, the compound transits to be converted into the crystal form A.

Figure 1:
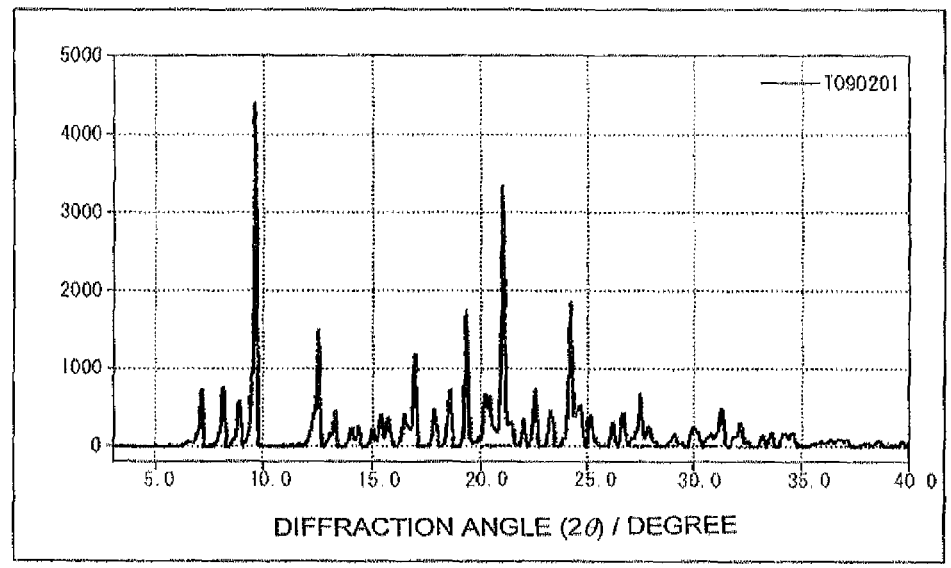
FIG. 1 is a powder X-ray diffraction chart of the crystal form A.
Figure 2:
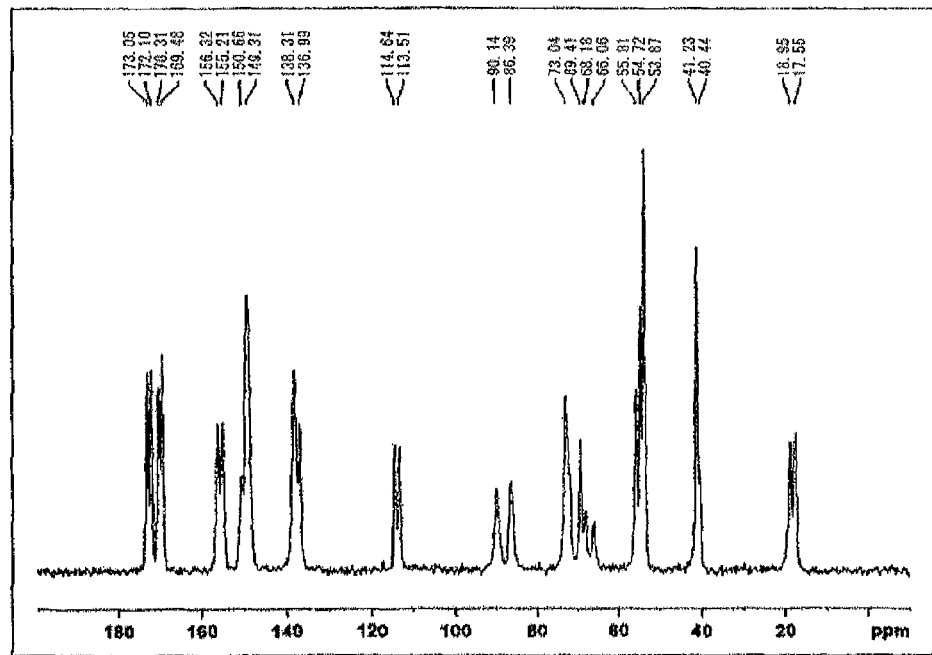
FIG. 2 is a $^{13}$C CP/TOSS NMR chart of the crystal form A.
Figure 3:
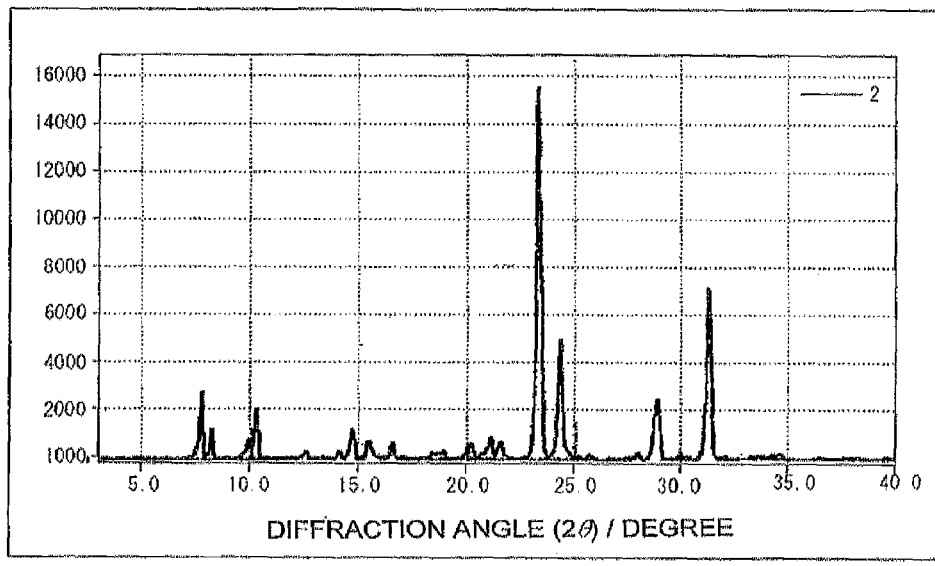
FIG. 3 is a powder X-ray diffraction chart of the crystal form B.
Figure 4:
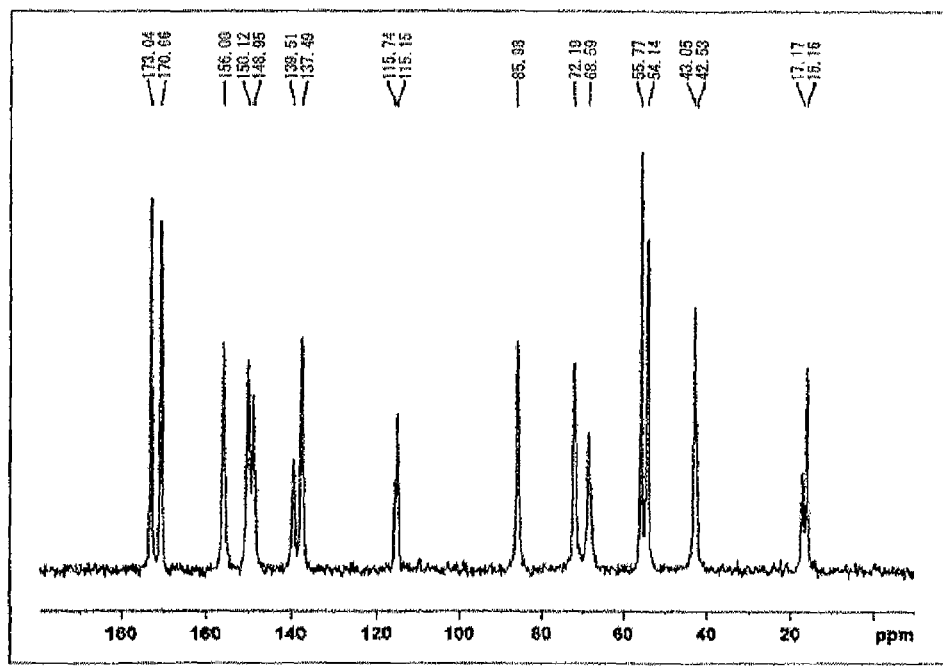
FIG. 4 is a $^{13}$C CP/TOSS NMR chart of the crystal form B.
Figure 5:
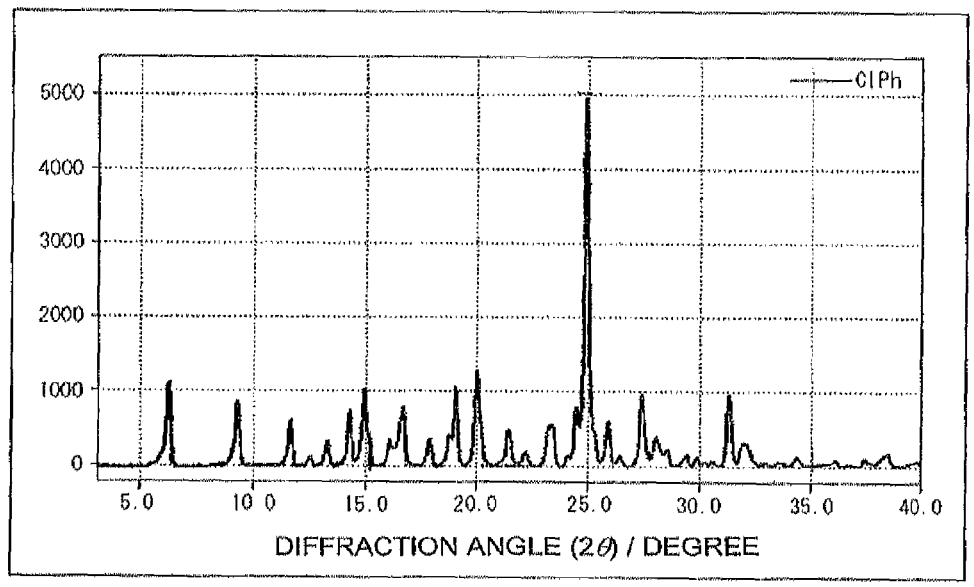
FIG. 5 is a powder X-ray diffraction chart of the crystal form C.
Figure 6:
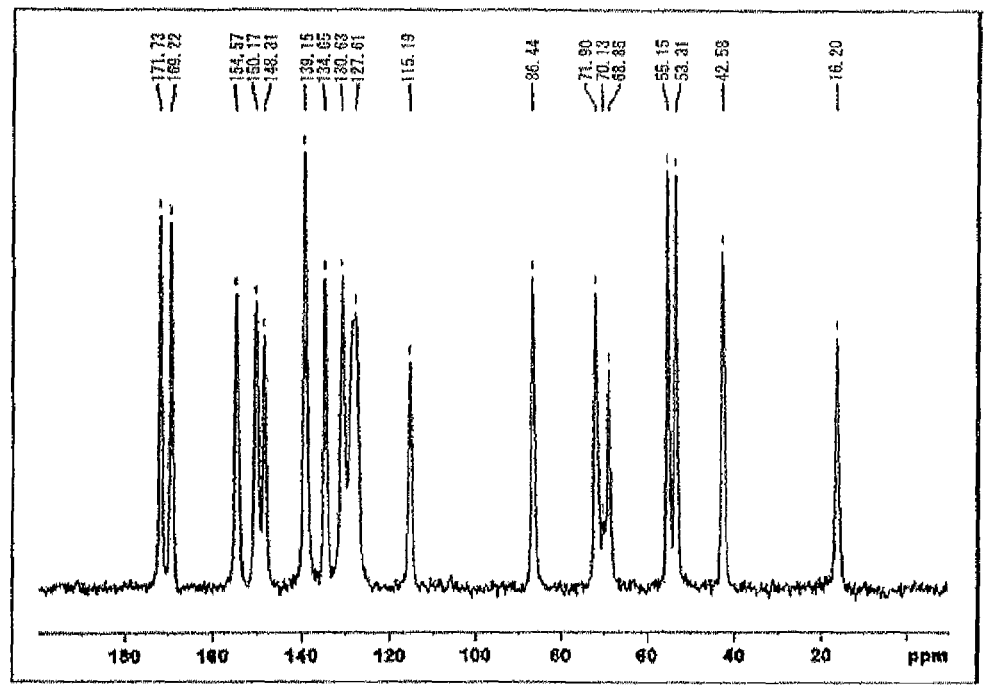
FIG. 6 is a $^{13}$C CP/TOSS NMR chart of the crystal form C.
Figure 7:
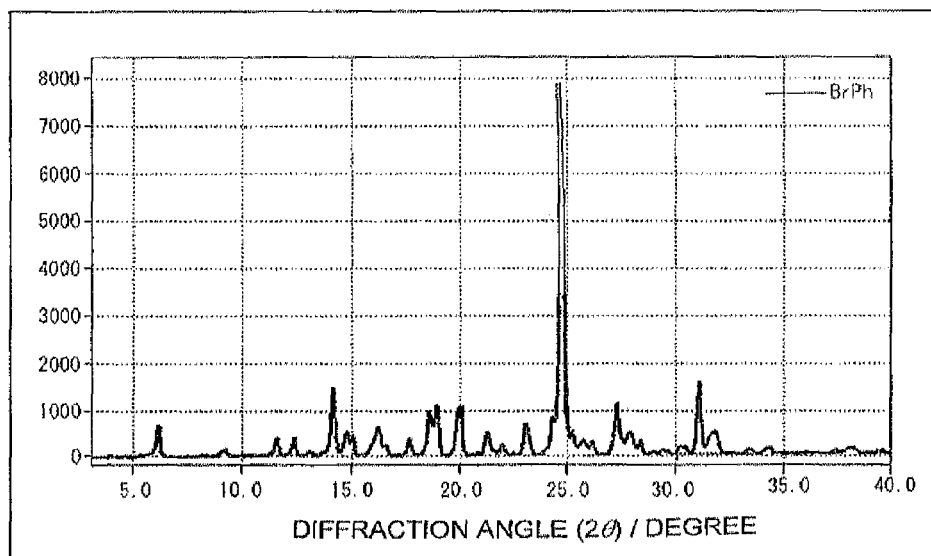
FIG. 7 is a powder X-ray diffraction chart of the crystal form D.
Figure 8:
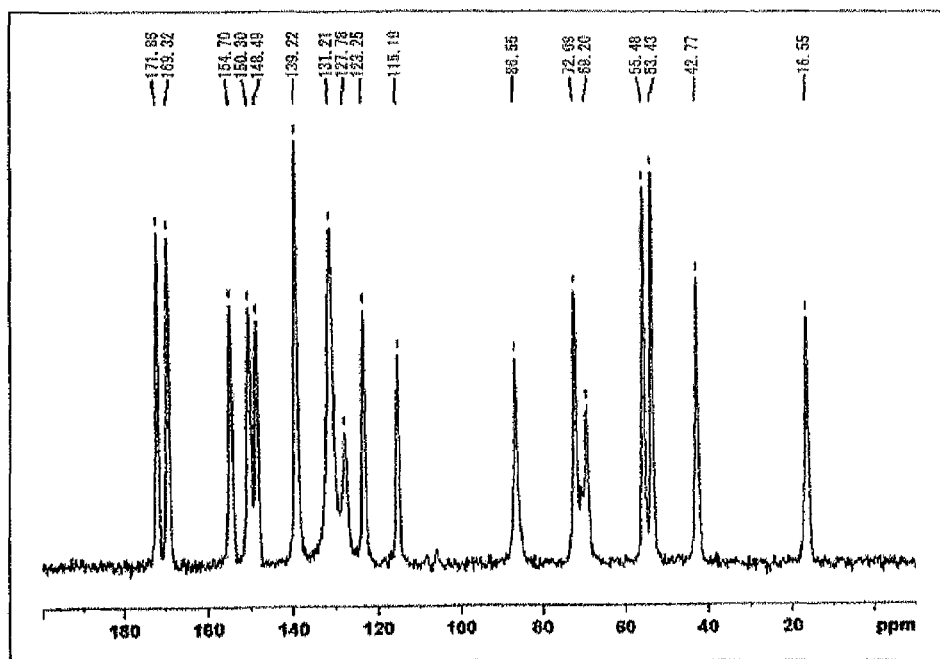
FIG. 8 is a $^{13}$C CP/TOSS NMR chart of the crystal form D.
Figure 9:
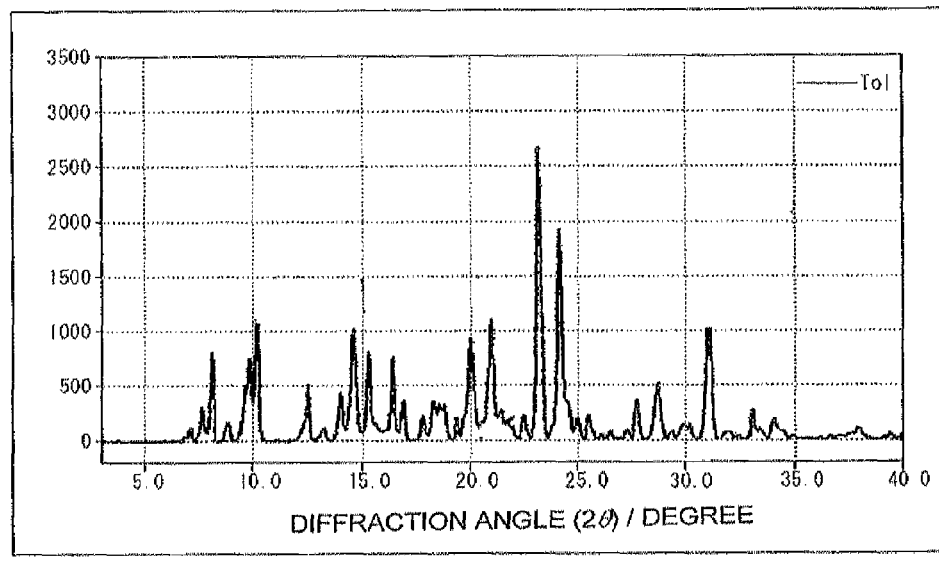
FIG. 9 is a powder X-ray diffraction chart of the crystal form E.
Figure 10:
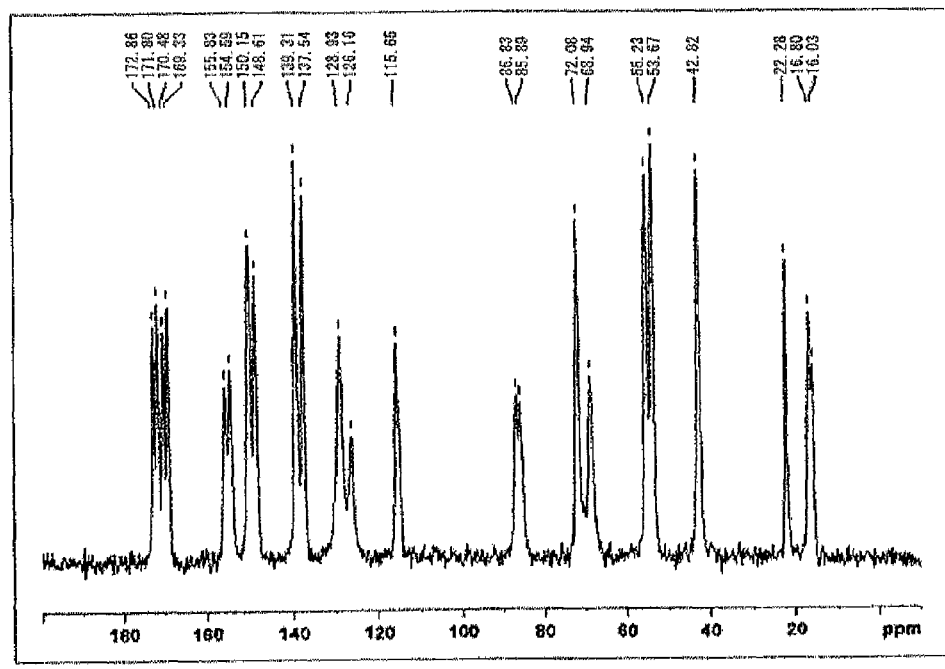
FIG. 10 is a $^{13}$C CP/TOSS NMR chart of the crystal form E.
Figure 11:
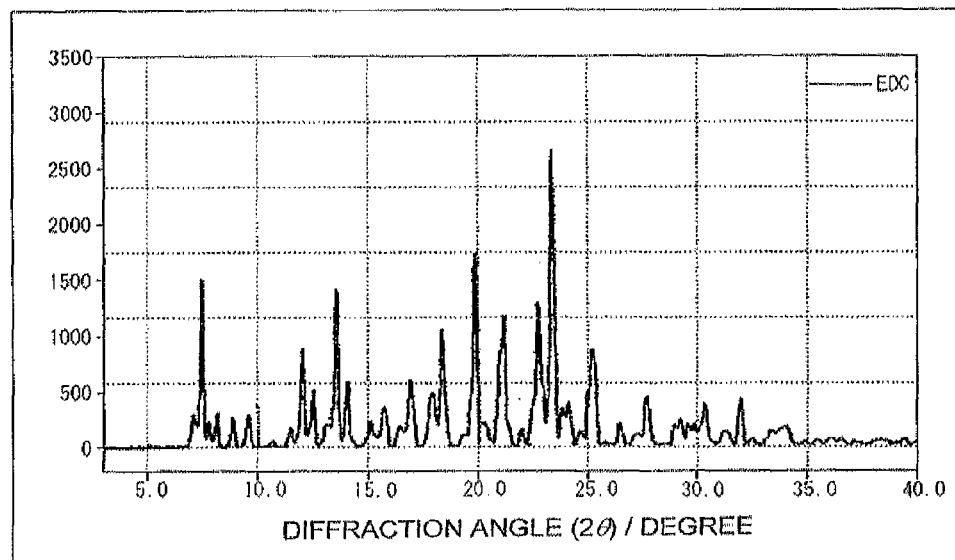
FIG. 11 is a powder X-ray diffraction chart of the crystal form F.
Figure 12:
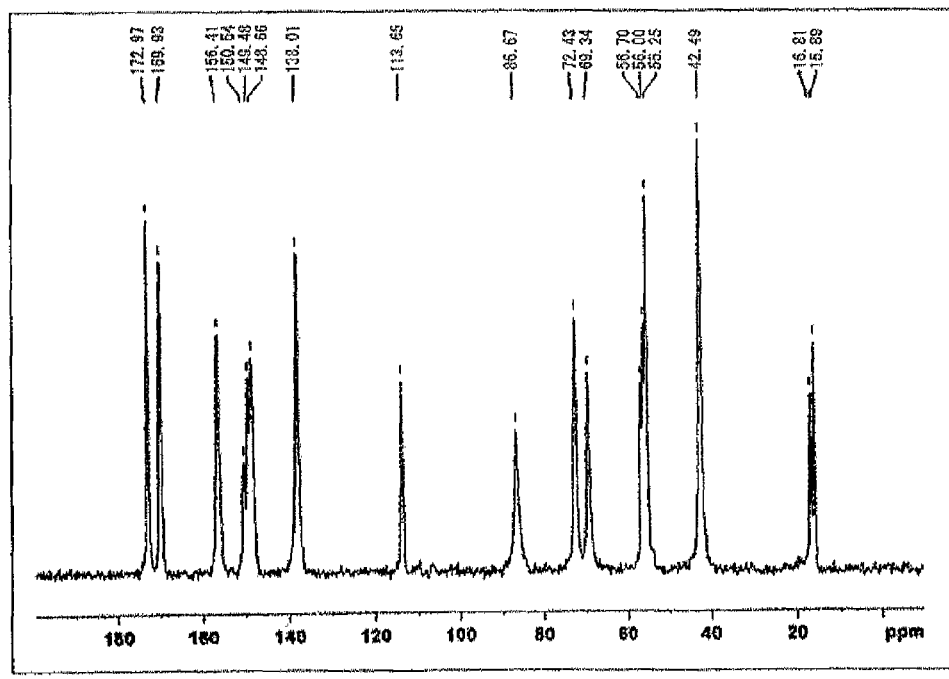
FIG. 12 is a $^{13}$C CP/TOSS NMR chart of the crystal form F.
Figure 13:
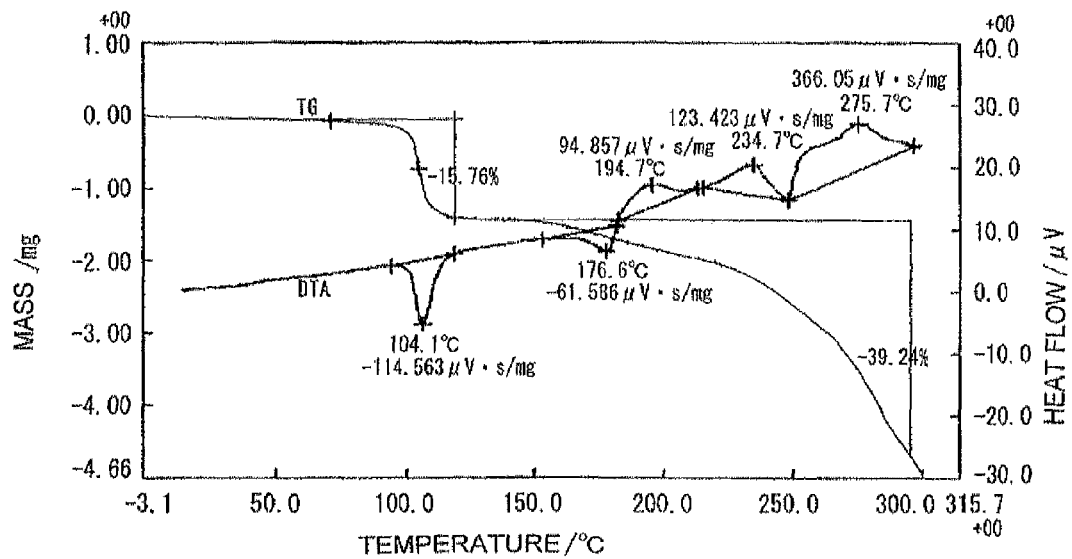
FIG. 13 is an endothermic peak chart 1 of the crystal form C.
Figure 14:
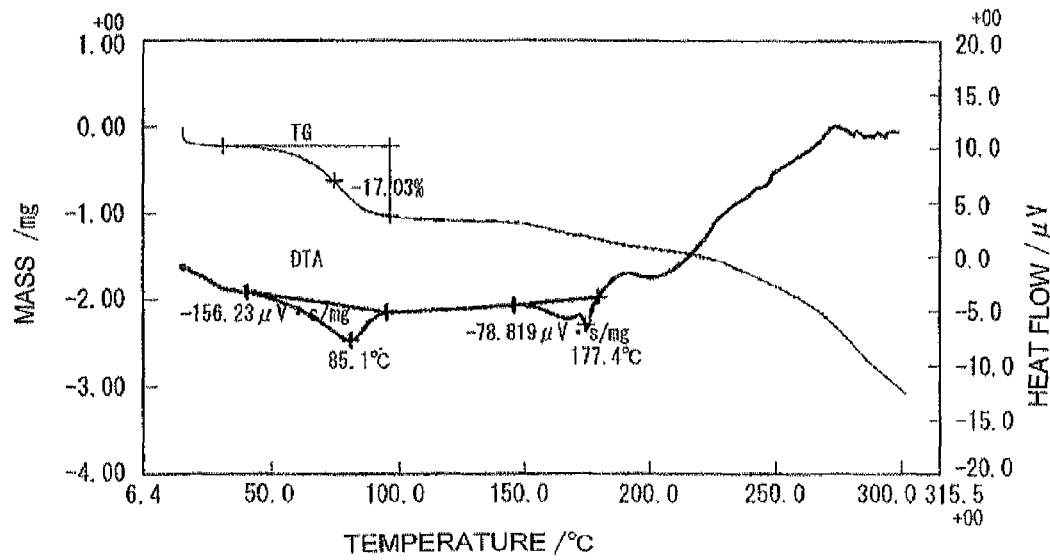
FIG. 14 is an endothermic peak chart 2 of the crystal form C.

The sulfonylurea compound of the crystal form C is a chlorobenzene solvate containing, in the crystal thereof, a chlorobenzene molecule, and may be obtained by stirring or by a crystallization operation in a chlorobenzene solvent or a solvent containing chlorobenzene. The sulfonylurea compound of the crystal form C has characteristic peaks at 2θ=6.24°, 9.24°, 11.56°, 12.44°, 13.16°, 14.16°, 14.80°, 15.92°, 16.52°, 17.72°, 18.56°, 18.96°, 19.88°, 21.36°, 22.12°, 23.28°, 24.40°, 24.92°, 25.84°, 27.40°, 28.00°, 28.48°, 31.24°, 31.88°, 34.32° in the powder X-ray diffraction, and has characteristic peaks at 16.20 ppm, 42.58 ppm, 53.31 ppm, 55.15 ppm, 68.85 ppm, 70.13 ppm, 71.90 ppm, 86.44 ppm, 115.19 ppm, 127.61 ppm, 130.63 ppm, 134.65 ppm, 139.15 ppm, 148.31 ppm, 150.17 ppm, 154.57 ppm, 169.22 ppm, 171.73 ppm in $^{13}$C CP/TOSS NMR. By heating or friction of the crystal form C, a chlorobenzene molecule is eliminated and the crystal form C transits to the crystal form A or B. Although in the differential thermal analysis thereof, there are confirmed an endothermic peak and a loss of the sample weight indicating the elimination of a chlorobenzene molecule, the sulfonylurea compound of the crystal form C has two types of patterns, namely, a pattern shown in FIG. 13 in which an endothermic peak is at a temperature of about 104 to 110° C. and a pattern shown in FIG. 14 in which an endothermic peak is at a temperature of about 85° C. The former is produced with advantageous reproducibility when the former is crystallized at 30° C. or more in a chlorobenzene solvent, and by eliminating a chlorobenzene molecule therefrom under heating/pressure-reducing condition, the former transits to the crystal form A. The latter is obtained with advantageous reproducibility when the latter is crystallized at −15° C. or less in a chlorobenzene solvent, and by eliminating a chlorobenzene molecule therefrom under heating/pressure-reducing condition, the latter transits to the crystal form B. At this time, also by crystallization by cooling the chlorobenzene solution thereof, a desired crystal form C is obtained. However, by a dropping crystallization method in which a heated chlorobenzene solution thereof is dropped into a cooled chlorobenzene solvent, with more advantageous reproducibility, the sulfonylurea compound of the latter crystal form C can be obtained. When the crystallization is performed at −10 to 20° C. in a chlorobenzene solvent, a mixture of two types of crystal form C is produced. This mixture is converted into a mixture of the crystal form A and the crystal form B by the elimination of a chlorobenzene molecule under heating/pressure-reducing condition.

The sulfonylurea compound of the crystal form D is a bromobenzene solvate containing, in the crystal thereof, a bromobenzene molecule, and may be obtained by stirring or by a crystallization operation in a bromobenzene solvent or a solvent containing bromobenzene. The sulfonylurea compound of the crystal form D has characteristic peaks at 2θ=14.43°, 11.52°, 12.28°, 14.04°, 14.64°, 16.12°, 17.52°, 18.8°, 19.84°, 21.16°, 23.00°, 24.72°, 25.64°, 26.08°, 27.24°, 27.84°, 28.32°, 31.04°, 31.76° in the powder X-ray diffraction, and has characteristic peaks at 16.55 ppm, 42.77 ppm, 53.43 ppm, 55.48 ppm, 69.20 ppm, 72.09 ppm, 86.55 ppm, 115.19 ppm, 123.25 ppm, 127.78 ppm, 131.21 ppm, 139.22 ppm, 148.49 ppm, 150.30 ppm, 154.70 ppm, 169.32 ppm, 171.86 ppm in $^{13}$C CP/TOSS NMR. By heating the crystal form D, a bromobenzene molecule is eliminated and the crystal form D transits to the crystal form A. In the differential thermal analysis thereof, there are confirmed an endothermic peak and a loss of the sample weight indicating the elimination of a bromobenzene molecule at about 94° C.

The sulfonylurea compound of the crystal form E is a toluene solvate containing, in the crystal thereof, a toluene molecule, and may be obtained by stirring or by a crystallization operation in a toluene solvent or a solvent containing toluene. The sulfonylurea compound of the crystal form E has characteristic peaks at 2θ=7.64°, 8.12°, 8.84°, 9.80°, 10.16°, 12.44°, 13.96°, 14.52°, 15.24°, 16.36°, 16.84°, 17.72°, 18.24°, 18.76°, 19.32°, 20.00°, 21.00°, 21.44°, 22.48°, 23.24°, 24.2°, 25.04°, 25.56°, 27.84°, 28.8°, 31.2°, 33.12°, 34.12° in the powder X-ray diffraction, and has characteristic peaks at 16.03 ppm, 16.80 ppm, 22.28 ppm, 42.82 ppm, 53.67 ppm, 55.23 ppm, 68.94 ppm, 72.08 ppm, 85.89 ppm, 86.83 ppm, 115.65 ppm, 126.16 ppm, 128.93 ppm, 137.54 ppm, 139.31 ppm, 148.61 ppm, 150.15 ppm, 154.59 ppm, 155.83 ppm, 169.33 ppm, 170.48 ppm, 171.80 ppm, 172.86 ppm in $^{13}$C CP/TOSS NMR. By heating or friction of the crystal form E, a toluene molecule is eliminated and the crystal form E transits to the crystal form A. In the differential thermal analysis thereof, there are confirmed an endothermic peak and a loss of the sample weight indicating the elimination of a toluene molecule at about 71° C.

The sulfonylurea compound of the crystal form F is a 1,2-dichloroethane solvate containing, in the crystal thereof, a 1,2-dichloroethane molecule, and may be obtained by stirring or by a crystallization operation in a 1,2-dichloroethane solvent or a solvent containing 1,2-dichloroethane. The sulfonylurea compound of the crystal form F has characteristic peaks at 2θ=7.00°, 7.48°, 8.16°, 8.84°, 9.56°, 11.44°, 12.00°, 12.48°, 13.04°, 13.52°, 14.04°, 15.08°, 15.68°, 16.36°, 16.88°, 17.88°, 18.36°, 19.88°, 20.36°, 21.2°, 22.00°, 22.80, 23.48°, 24.20°, 25.28°, 26.56°, 27.84°, 29.32°, 29.80°, 30.48°, 32.12°, 34.12° in the powder X-ray diffraction, and has characteristic peaks at 15.89 ppm, 16.81 ppm, 42.49 ppm, 55.25 ppm, 56.00 ppm, 56.70 ppm, 69.34 ppm, 72.43 ppm, 86.67 ppm, 113.65 ppm, 138.01 ppm, 148.66 ppm, 149.48 ppm, 150.54 ppm, 156.41 ppm, 169.93 ppm, 172.97 ppm in $^{13}$C CP/TOSS NMR. By heating or friction of the crystal form F, a 1,2-dichloroethane molecule is eliminated and the crystal form F transits to the crystal form A. In the differential thermal analysis thereof, there are confirmed an endothermic peak and a loss of the sample weight indicating the elimination of an EDC molecule at about 94° C.

The solvent is not particularly limited so long as the solvent is a solvent capable of dissolving the compound of Formula (1) and capable of existing stably in the resultant solution. Examples of the solvent include: alcohols such as methanol, ethanol, propanol, and butanol; ethers such as diethyl ether, tetrahydrofuran, dimethoxyethane, dioxane, and cyclopentyl methyl ether; aromatic hydrocarbons such as benzene, xylene, toluene, and o-xylene; aliphatic hydrocarbons such as pentane, hexane, cyclohexane, heptane, and petroleum ethers; halogenated hydrocarbons such as dichloromethane, chloroform, 1,2-dichloroethane, and carbon tetrachloride; esters such as ethyl acetate and butyl acetate; ketones such as acetone and methyl ethyl ketone; nitriles such as acetonitrile and propionitrile; amides such as N,N-dimethylformamide, N,N-dimethylacetamide, N-methylpyrrolidone, and N,N'-dimethylimidazolinone; and dimethylsulfoxide. These solvents may be used individually or in combination of two or more types thereof. Particularly, for the production of the sulfonylurea compound of the crystal form A, o-xylene or a solvent mixture of o-xylene and heptane is preferred; for the production of the sulfonylurea compound of the crystal form C, chlorobenzene is preferred; for the production of the sulfonylurea compound of the crystal form D, bromobenzene is preferred; for the production of the sulfonylurea compound of the crystal form E, toluene is preferred; and for the production of the sulfonylurea compound of the crystal form F, 1,2-dichloroethane is preferred.

The heating temperature is preferably 20° C. or more, further preferably 50° C. or more.

The temperature for the crystallization filtration is preferably 50° C. or less. Particularly when a crystal form B in a high purity is desired, the temperature is further preferably −15° C. or less.

Examples of the crystallization method include cooling crystallization in which the sample is heating-dissolved in a solvent and the resultant solution is cooled to precipitate a crystal, and dropping crystallization in which a solution of the sample is dropped into a cooled solvent or a poor solvent.

Each crystal form can be produced by any one of these crystallization methods. However, when a crystal form C that transits to the crystal form B among crystal forms C is produced, the latter method is more preferred in terms that the temperature for crystal precipitation can be easily controlled.

When a crystal is precipitated, by adding a small amount of the crystal, the timing for precipitation of the crystal can be adjusted. Although the crystal form of the crystal to be added at this time may be any crystal form, a crystal form the same as the desired crystal form is desirably added.

Heating is preferably performed in an atmosphere of an inert gas.

Examples of the inert gas include nitrogen, argon, xenon, and helium.

Next, the suspension of a composition (hereinafter, called "composition of the present invention") containing a sulfonylurea compound that is in the crystal form A of the sulfonylurea compound of Formula (1) of the present invention is described in detail.

The composition of the present invention can use, as a dispersion medium thereof, water or an organic liquid difficultly dissolving the crystal form A. Examples of the organic liquid include alcohols such as ethylene glycol, diethylene glycol, propylene glycol, dipropylene glycol, and isopropanol; ethers such as butylcellosolve; ketones such as cyclohexanone; esters such as γ-butyrolactone; acid amides such as N-methylpyrrolidone and N-octylpyrrolidone; aromatic hydrocarbons such as xylene, alkylbenzene, phenylxylylethane, and alkylnaphthalene; aliphatic hydrocarbons such as a machine oil, n-paraffin, isoparaffin, and naphthene; mixtures of aromatic hydrocarbons and aliphatic hydrocarbons such as kerosene; and fats and oils such as soybean oil, linseed oil, rapeseed oil, coconut oil, cottonseed oil, and castor oil.

The content of the sulfonylurea compound of the crystal form A is ordinarily 0.1 to 50 parts by weight, more preferably 1 to 30 part(s) by weight, relative to 100 parts by weight of the composition of the present invention.

The composition of the present invention suppresses aging decomposition of the sulfonylurea compound of Formula (1). In the composition of the present invention, for thoroughly suppressing aging decomposition of the sulfonylurea compound of Formula (1), the content of the crystal form A in the compound is preferably 10 to 100% by weight, more preferably 30 to 100% by weight, further preferably 50 to 100% by weight.

The composition of the present invention can also contain, besides the sulfonylurea compound of Formula (1), further one or more type(s) of publicly known pesticide such as a herbicide, an insecticide, a miticide, a nematicide, an antiviral agent, a plant growth regulator, a bactericide, a synergist, an attractant, and a repellent, and when the composition of the present invention contains such a pesticide, the composition may exhibit furthermore excellent pest control effect. As the publicly known pesticide, a herbicide is particularly preferred. Specific examples of the general name of the herbicide are as follows.

Herbicides: pyrazosulfuron ethyl, halosulfuron methyl, bensulfuron methyl, imazosulfuron, azimsulfuron, cinosulfuron, cyclosulfamuron, ethoxysulfuron, quinoclamin, metazosulfuron, pyraclonil, aminocyclopyrachlor, tefuryltrione, mesotrione, pyrimisulfan, penoxsulam, aminopyralid, bencarbazone, orthosulfamrun, flucetosulfuron, monosulfuron, monosulfuron-methyl, pinoxaden, propoxycarbazone-sodium, pyrasulfotole, pyroxasulfone, pyroxsulam, tembotrione, thiencarbazone-methyl, topramezon, metamitron, esprocarb, benthiocarb, molinate, dimepiperate, pyributicarb, mefenacet, butachlor, pretilachlor, thenylchlor, bromobutide, etobenzanid, dymron, cumyluron, bentazone, pyriftalid, bispyribac, a salt of bentazone, 2,4-D, a salt of 2,4-D, an ester of 2,4-D, MCP, a salt of MCP, an ester of MCP, MCPB, a salt of MCPB, an ester of MCPB, phenothiol (MCPA-thioethyl), clomeprop, naproanilide, oxadiazon, pyrazolate, pyrazoxyfen, benzofenap, oxadiargyl, dimethametryn, simetryn, piperophos, anilofos, butamifos, bensulide, dithiopyr, pyriminobac methyl, CNP, chlormethoxynil, cyhalofop butyl, bifenox, cafenstrole, pentoxazone, indanofan, oxaziclomefone, fentrazamide, butenachlor, ACN, benzobicyclon, benfuresate, cimmethylin, simazine, diuron, chloro IPC (chlorpropham), atrazine, alachlor, isouron, chlorphtalim, cyanazin, trifluralin, butamifos, quinclorac, propyzamide, prometryn, pendimethalin, metolachlor, metribuzin, linuron, lenacil, propanil, MCPA, ioxynil (ioxynil octanoate), asulam, quizalofop-ethyl, propaquizafop, quizalofop-tefuryl, sethoxydim, thifensulfuron-methyl, fenoxaprop-ethyl, phenmedipham, fluazifop-butyl, bentazone, SAP (bensulide), TCTP (chorthal-dimethyl, tetorachlorothiophene), amiprophosmethyl, ametryn, isoxaben, orbencarb, karbutilate, dithiopyr, siduron, thiazafluron, napropamide, prodiamine, bethrodine, methyl dymron, 2,4-PA, MCPPA, flazasulfuron, metsulfuron-methyl, imazaquin, imazapyr, tetrapion (flupropanate), tebuthiuron, bromacil, hexazinone, glyphosate-ammonium, glyphosate-iso-propylammonium, glyphosate-trimesium, glyphosate-sodium, glyphosate-potassium, bialaphos, glufosinate-ammonium, OK-701 (test name), HOK-201 (test name), TH-547 (test name), and MCC.

In the composition of the present invention, if necessary, a surfactant may also be blended. Examples of the surfactant include (A), (B), (C), (D), and (E) below.

(A) Nonionic Surfactant (A-1) Polyethylene glycol-based surfactant: for example, polyoxyethylene alkyl (for example, $C_{8-18}$) ether, ethylene oxide-adduct of alkylnaphthol, polyoxyethylene (mono- or di-)alkyl (for example, $C_{8-12}$) phenyl ether, formalin condensate of polyoxyethylene (mono- or di-)alkyl (for example, $C_{8-12}$) phenyl ether, polyoxyethylene (mono-, di-, or tri-) phenyl phenyl ether, polyoxyethylene (mono-, di-, or tri-) benzyl phenyl ether, polyoxypropylene (mono-, di-, or tri-) benzyl phenyl ether, polyoxyethylene (mono-, di-, or tri-) styryl phenyl ether, polyoxypropylene (mono-, di-, or tri-) styryl phenyl ether, a polymer of polyoxyethylene (mono-, di-, or tri-)styryl phenyl ether, polyoxyethylene-polyoxypropylene (mono-, di-, or tri-) styryl phenyl ether, a polyoxyethylene-polyoxypropylene block polymer, alkyl (for example, $C_{8-18}$) polyoxyethylene-polyoxypropylene block polymer ether, alkyl (for example, $C_{8-12}$) phenyl polyoxyethylene-polyoxypropylene block polymer ether, polyoxyethylene bisphenyl ether, polyoxyethylene resin acid ester, polyoxyethylene aliphatic acid (for example, $C_{8-18}$) monoester, polyoxyethylene aliphatic acid (for example, $C_{8-18}$) diester, polyoxyethylenesorbitan (mono-, di-, or tri-)aliphatic acid (for example, $C_{8-18}$) ester, glycerol aliphatic acid ester ethylene oxide-adduct, castor oil ethylene oxide-adduct, hydrogenated castor oil ethylene oxide-adduct, alkyl (for example, $C_{8-18}$) amine ethylene oxide-adduct, and aliphatic acid (for example, $C_{8-18}$) amide ethylene oxide-adduct.

(A-2) Polyhydric alcohol-based surfactant: for example, glycerol aliphatic acid ester, polyglycerin aliphatic acid ester, pentaerythritol aliphatic acid ester, sorbitol aliphatic acid (for example, $C_{8-18}$) ester, sorbitan (mono-, di-, or tri-)aliphatic acid (for example, $C_{8-18}$) ester, sucrose aliphatic acid ester, polyhydric alcohol alkyl ether, alkyl glycoside, alkyl polyglycoside, and aliphatic acid alkanolamide.

(A-3) Acetylene-based surfactant: for example, acetylene glycol, acetylene alcohol, ethylene oxide-adduct of acetylene glycol, and ethylene oxide-adduct of acetylene glycol.

(B) Anionic Surfactant (B-1) Carboxylic acid-based surfactant: for example, polyacrylic acid, polymethacrylic acid, polymaleic acid, polymaleic anhydride, a copolymer of maleic acid or maleic anhydride with olefin (such as isobutylene and diisobutylene), a copolymer of acrylic acid with itaconic acid, a copolymer of methacrylic acid with itaconic acid, a copolymer of maleic acid or maleic anhydride with styrene, a copolymer of acrylic acid with methacrylic acid, a copolymer of acrylic acid with acrylic acid methyl ester, a copolymer of acrylic acid with vinyl acetate, a copolymer of acrylic acid with maleic acid or maleic anhydride, polyoxyethylene alkyl (for example, $C_{8-18}$) ether acetic acid, N-methyl-aliphatic acid (for example, $C_{8-18}$) sarcosinate, carboxylic acid such as resin acid and aliphatic acid (for example, $C_{8-18}$), and salts of the carboxylic acid.

(B-2) Sulfuric acid ester-based surfactant: for example, alkyl (for example, $C_{8-18}$) sulfuric acid ester, polyoxyethylene alkyl (for example, $C_{8-18}$) ether sulfuric acid ester, polyoxyethylene (mono- or di-)alkyl (for example, $C_{8-12}$) phenyl ether sulfuric acid ester, sulfuric acid ester of a polymer of polyoxyethylene (mono- or di-)alkyl (for example, $C_{8-12}$) phenyl ether, polyoxyethylene (mono-, di-, or tri-)phenyl phenyl ether sulfuric acid ester, polyoxyethylene (mono-, di-, or tri-)benzyl phenyl ether sulfuric acid ester, polyoxyethylene (mono-, di-, or tri-)styryl phenyl ether sulfuric acid ester, sulfuric acid ester of a polymer of polyoxyethylene (mono-, di-, or tri-)styryl phenyl ether, sulfuric acid ester of a polyoxyethylene-polyoxypropylene block polymer, sulfated oil, sulfated aliphatic acid ester, sulfuric acid ester of sulfated aliphatic acid with sulfated olefin or the like, and salts of the sulfuric acid esters.

(B-3) Sulfonic acid-based surfactant: for example, paraffin (for example, $C_{8-22}$) sulfonic acid, alkyl (for example, $C_{8-12}$) benzene sulfonic acid, formalin condensate of alkyl (for example, $C_{8-12}$) benzene sulfonic acid, formalin condensate of cresol sulfonic acid, α-olefin (for example, $C_{8-16}$) sulfonic acid, dialkyl (for example, $C_{8-12}$) sulfosuccinic acid, lignin sulfonic acid, polyoxyethylene (mono- or di-)alkyl (for example, $C_{8-12}$) phenyl ether sulfonic acid, polyoxyethylene alkyl (for example, $C_{8-18}$) ether sulfosuccinic acid half ester, naphthalene sulfonic acid, (mono- or di-)alkyl (for example, $C_{1-6}$) naphthalene sulfonic acid, formalin condensate of naphthalene sulfonic acid, formalin condensate of (mono- or di-)alkyl (for example, $C_{1-6}$) naphthalene sulfonic acid, formalin condensate of creosote oil sulfonic acid, alkyl (for example, $C_{8-12}$) diphenyl ether disulfonic acid, Igepon T (trade name), sulfonic acid such as polystyrene sulfonic acid and a copolymer of styrene sulfonic acid with methacrylic acid, and salts of the sulfonic acids.

(B-4) Phosphoric acid ester-based surfactant: for example, alkyl (for example, $C_{8-12}$) phosphoric acid ester, polyoxyethylene alkyl (for example, $C_{8-18}$) ether phosphoric acid ester, polyoxyethylene (mono- or di-)alkyl (for example, $C_{8-12}$) phenyl ether phosphoric acid ester, phosphoric acid ester of a polymer of polyoxyethylene (mono-, di-, or tri-)alkyl (for example, $C_{8-12}$) phenyl ether, polyoxyethylene (mono-, di-, or tri-)phenyl phenyl ether phosphoric acid ester, polyoxyethylene (mono-, di-, or tri-)benzyl phenyl ether phosphoric acid ester, polyoxyethylene (mono-, di-, or tri-)styryl phenyl ether phosphoric acid ester, phosphoric acid ester of a polymer of polyoxyethylene (mono-, di-, or tri-)styryl phenyl ether, phosphoric acid ester of a polyoxyethylene-polyoxypropylene block polymer, phosphoric acid ester such as phosphatidylcholine, phosphatidylethanolimine, and condensed phosphoric acid (such as tripolyphosphoric acid), and salts of the phosphoric acid esters.

Examples of the counter ion of the salts in (B-1) to (B-4) include alkali metals (such as lithium, sodium, and potassium), alkaline earth metals (such as calcium and magnesium), and ammonium and various amines (such as alkylamine, cycloalkylamine, and alkanolamine).

(C) Cationic Surfactant for example, alkylamine, an alkyl quaternary ammonium salt, ethylene oxide-adduct of alkylamine, and ethylene oxide-adduct of an alkyl quaternary ammonium salt.

(D) Amphoteric Surfactant (D-1) Betaine-type surfactant: for example, alkyl (for example, $C_{8-18}$)dimethylamino acetic acid betaine, acyl (for example, $C_{8-18}$)aminopropyldimethylamino acetic acid betaine, alkyl (for example, $C_{8-18}$)hydroxysulfo betaine, and 2-alkyl (for example, $C_{8-18}$)—N-carboxymethyl-N-hydroxyethylimidazolinium betaine.

(D-2) Amino acid-type surfactant: for example, alkyl (for example, $C_{8-18}$)aminopropionic acid, alkyl (for example, $C_{8-18}$)aminodipropionic acid, and N-acyl (for example, $C_{8-18}$)—N'-carboxyethyl-N'-hydroxyethylethylenediamine.

(D-3) Amine oxide-type surfactant: for example, alkyl (for example, $C_{8-18}$)dimethylamine oxide and acyl (for example, $C_{8-18}$)aminopropyldimethylamine oxide.

(E) Other Surfactants (E-1) Silicon-based surfactant: for example, a polyoxyethylene-methylpolysiloxane copolymer, a polyoxypropylene-methylpolysiloxane copolymer, and a poly(oxyethylene-oxypropylene)-methylpolysiloxane copolymer.

(E-2) Fluorinated surfactant: for example, perfluoroalkenylbenzenesulfonic acid salts, perfluoroalkylsulfonic acid salts, perfluoroalkylcarboxylic acid salts, perfluoroalkenyl polyoxyethylene ether, perfluoroalkyl polyoxyethylene ether, and perfluoroalkyltrimethyl ammonium salts.

These surfactants may be used individually or in mixture of two or more types thereof and the mixing ratio can be freely selected. Although the content of the surfactant in the composition of the present invention can be accordingly selected, the content is preferably in a range of 0.1 to 20 parts by weight, relative to 100 parts by weight of the composition of the present invention.

In the composition of the present invention, further various assistants may be blended. Examples of the usable assistants include a thickener, an organic solvent, an antifreezing agent, an antifoamer, an anti-bacterial/anti-mold agent, and a colorant, and specific examples thereof include the followings.

The thickener is not particularly limited, and as the thickener, organic and inorganic natural, synthetic, and semi-synthetic products can be used. Specific examples thereof include hetero-polysaccharides such as xanthan gum, welan gum, and rhamsan gum; water-soluble polymer compounds such as polyvinyl alcohol, polyvinyl pyrrolidone, polyacrylic acid, sodium polyacrylate, and polyacrylamide; cellulose derivatives such as methylcellulose, carboxymethylcellulose, carboxyethylcellulose, hydroxyethylcellulose, and hydroxypropylcellulose; and smectite-type clay minerals such as montmorillonite, saponite, hectorite, bentonite, laponite, and synthetic smectite. These thickeners may be used individually or in mixture of two or more types thereof and the mixing ratio can be freely selected. These thickeners may be added as they are or as a dispersion in which the thickener is dispersed in water beforehand. The content of the thickener in the composition of the present invention can also be freely selected.

Examples of the organic solvent include alcohols such as ethylene glycol, diethylene glycol, propylene glycol, dipropylene glycol, and isopropanol; ethers such as butylcellosolve; ketones such as cyclohexanone; esters such as γ-butyrolactone; acid amides such as N-methylpyrrolidone and N-octylpyrrolidone; aromatic hydrocarbons such as xylene, alkylbenzene, phenylxylylethane, and alkylnaphthalene; aliphatic hydrocarbons such as a machine oil, n-paraffin, isoparaffin, and naphthene; mixtures of aromatic hydrocarbons and aliphatic hydrocarbons such as kerosene; and fats and oils such as soybean oil, linseed oil, rapeseed oil, coconut oil, cottonseed oil, and castor oil.

Examples of the antifreezing agent include ethylene glycol, diethylene glycol, propylene glycol, and glycerin. Preferred are propylene glycol and glycerin. The content of the antifreezing agent in the composition of the present invention can also be freely selected.

In the composition of the present invention, further an antifoamer such as a silicone-based emulsion, an anti-bacterial/anti-mold agent, a colorant, and the like may also be blended.

Although the production method of the composition of the present invention is not particularly limited, the composition can be obtained by a method including: adding the above components to a dispersion medium; and mixing the resultant dispersion by a stirrer. If necessary, a pesticide active ingredient, a surfactant, and other assistants may be individually or in mixture pulverized by a dry or wet grinding mill.

Dry grinding can be performed by a hammer mill, a pin mill, a jet mill, a ball mill, a roll mill, or the like. Pulverization by wet grinding can be performed by a wet grinding mill such as an inline mill and a beads mill.

The composition of the present invention can be applied, for example, by a method in which a stock solution of the composition or a diluted solution prepared by diluting the stock solution with water by around 50 to 5,000 times is prepared and the stock solution or the diluted solution is sprayed over a crop, a tree, or a soil on which they grow using a sprayer, or by a method in which a stock solution of the composition or a diluted solution prepared by diluting the stock solution with water by around 2 to 100 times is prepared and the stock solution or the diluted solution is sprayed from the air using a helicopter.

EXAMPLES

Hereinafter, the present invention is described further in detail by specifically describing the production examples of the crystal of the compound of the present invention as Examples, which should not be construed as limiting the scope of the present invention.

Here, measuring conditions are as follows.

$^{13}C$ CP/TOSS NMR Measuring Conditions

Apparatus: 500 MHz FTNMR spectrophotometer (manufactured by Bruker Corporation; AVANCE III 500)
Probe: 4 mm CP/MAS probe
Measuring method: CP/TOSS method
Observed nucleus: $^{13}C$ Observation frequency: 125.8 MHz
Range of observation frequency: 38 kHz
Data point: 2 k
Number of revolutions of test tube: 8 kHz
Contact time: 3.5 ms
Waiting time: 20 seconds
Number of integrations: 256 times Powder X-Ray Diffraction Measuring Conditions Apparatus: MXLabo (manufactured by Mac Science Corporation (present: Bruker AXS, Inc.))
Ray source: Cu
Wavelength: 1.54056 A
Goniometer: vertical-type goniometer
Tube voltage: 40.0 kV
Tube current: 30 mA
Measuring method: continuous method
Data range: 3.0400 to 40.0000 deg
Scanning axis: 2θ/θ
Sampling interval: 0.0400 deg
Scanning rate: 3.600 deg/min.
Emission slit: 1.00 deg
Scattering slit: 1.00 deg
Receiving slit: 0.15 mm
RSM: 0.80 mm Differential Thermal Analysis Measuring Conditions Apparatus: TG 8120 (manufactured by Rigaku Corporation)
Temperature elevation: 20° C. to 300° C. at an elevation rate of 5° C./min
Atmosphere: Air
Reference: $Al_2O_3$
Vessel: Al vessel
Sampling: 1 sec Production Example 1

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form C) (No. 1)

0.4 g of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) was dissolved in 9 g of chlorobenzene at 80° C. The resultant solution was cooled down to 0° C. and was stirred for 1 hour. A precipitated crystal was filtered and a liquid in the crystal surface was sucked off with a filter paper to recover 0.32 g of a wet product. As the result of the powder X-ray diffraction of the product, the crystal form of the obtained solid was C. As the result of the TG-DTA measurement of the product, an endothermic peak indicating the elimination of chlorobenzene was detected at 104° C.

Production Example 2

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) (No. 2)

0.3 g of the crystal form C produced in Production Example 1 was heated at 80° C. under 2 mmHg for 5 hours to be dried under reduced pressure to obtain 0.21 g of a dry product. As the result of the powder X-ray diffraction of the product, the crystal form after drying was A.

Production Example 3

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form C) (No. 2)

30 g of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) was dissolved in 225 g of chlorobenzene at 80° C. The resultant solution was gradually dropped into 80 g of chlorobenzene cooled down to −20° C. so that the temperature of the resultant reaction mixture did not exceed −15° C. The resultant reaction mixture was stirred at −20° C. for 30 minutes and a precipitated crystal was filtered, followed by sucking off a liquid in the crystal surface with a filter paper to recover 28.2 g of a wet product. As the result of the powder X-ray diffraction of the product, the crystal form of the obtained solid was the crystal form C. As the result of the TG-DTA measurement of the product, an endothermic peak indicating the elimination of chlorobenzene was detected at 86° C.

Production Example 4

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form B)

28 g of the crystal form C produced in Example 3 was heated at 80° C. under 2 mmHg for 5 hours to be dried under reduced pressure to obtain 22.5 g of a dry product. As the result of the powder X-ray diffraction of the product, the crystal form after drying was B.

Production Example 5

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form D)

0.5 g of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) was dissolved in 8 g of bromobenzene at 80° C. The resultant solution was gradually dropped into 7 g of bromobenzene cooled down to 0° C. so that the temperature of the resultant reaction mixture did not exceed 3° C. The resultant reaction mixture was stirred at 0° C. for 30 minutes and a precipitated crystal was filtered, followed by sucking off a liquid in the crystal surface with a filter paper to recover 0.55 g of a wet product. As the result of the powder X-ray diffraction of the product, the crystal form of the obtained solid was D.

Production Example 6

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form E)

0.5 g of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) was dissolved in 8 g of toluene at 80° C. The resultant solution was cooled down to 0° C. and was stirred for 30 minutes. A precipitated crystal was filtered and a liquid in the crystal surface was sucked off with a filter paper to recover 0.43 g of a wet product. As the result of the powder X-ray diffraction of the product, the crystal form of the obtained solid was E.

Production Example 7

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) (No. 3)

28 g of the crystal form. E produced in Production Example 6 was heated at 80° C. under 2 mmHg for 5 hours to be dried under reduced pressure to obtain 22.5 g of a dry product. As the result of the powder X-ray diffraction of the product, the crystal form after drying was A.

Production Example 8

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form F)

1 g of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) was dissolved in 6 g of 1,2-dichloroethane at 80° C. The resultant solution was cooled down to 0° C. and was stirred for 30 minutes. A precipitated crystal was filtered and a liquid in the crystal surface was sucked off with a filter paper to recover 0.73 g of a wet product. As the result of the powder X-ray diffraction of the product, the crystal form of the obtained solid was F.

Production Example 9

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) (No. 4)

0.5 g of the crystal form F obtained in Production Example 8 was heated at 80° C. under 2 mmHg for 5 hours to be dried under reduced pressure to obtain 0.41 g of a dry product. As the result of the powder X-ray diffraction of the product, the crystal form after drying was A.

Production Example 10

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A) (No. 5)

1 g of the crystal form B obtained in Production Example 4 was suspended in 5 g of o-xylene and the resultant suspension was stirred at 80° C. for 5 hours. The resultant solution was cooled down, was stirred at 0° C. for 30 minutes, and was filtered to obtain g of a crystal. As the result of the powder X-ray diffraction of the crystal, the crystal form of the obtained crystal was A.

Production Example 11

Production of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide (crystal form A)

150 g (0.425 mol) of methyl 3-chloro-1-methyl-4-(5-methyl-5,6-dihydro-1,4,2-dioxazine-3-yl)-1H-pyrazole-5-ylsulfo nylcarbamate produced by a method described in International Publication No. WO 2005/104033 pamphlet and 69.27 g (0.447 mol) of 2-amino-4,6-dimethoxypyrimidine were charged into a reaction vessel equipped with a Deanstark tube, and thereto, 675 g of o-xylene and 225 g of heptane were added. The resultant reaction solution was subjected to pressure reduction to 45 kPa, was heated at 90° C. for 12 hours, and was then cooled down to 30° C. A crystal was filtered, was washed over with 150 g of o-xylene, and was dried under reduced pressure at 50° C. to obtain 191.76 g (purity: 97.0%, yield: 91.9%) of the subject compound. The obtained crystal was measured by the powder X-ray diffraction and it was confirmed that the crystal form thereof was A.

Next, Production Example and Test Example of the composition of the present invention are specifically described.

Production Example 12

Hereinafter, all of "parts" mean "parts by mass".
1. Preparation of Ground Slurry In 14.24 parts of water, 0.1 parts of Supragil MNS/90 (trade name; manufactured by Rhodia, Inc.; formalin condensate of sodium methylnaphthalenesulfonate), 0.1 parts of SURFYNOL 104PG50 (trade name; manufactured by Air Products and Chemicals, Inc.; 50% propylene glycol solution of 2,4,7,9-tetramethyl-5-decyne-4,7-diol), 0.25 parts of citric anhydride, 7.0 parts of propylene glycol, and 2.3 parts of the crystal form A of a sulfonylurea compound of Formula (1) were dispersed, and the resultant dispersion was wet-ground by a sand grinder (manufactured by AIMEX Co., Ltd.) using 0.8-1.2 mmφ glass beads to obtain 24 parts of a ground slurry.
2. Preparation of Dispersion Medium In 98.5 parts of water, 1 part of xanthan gum (KELZAN ASX) and 0.5 parts of Proxel GXL were dispersed to obtain 100 parts of a dispersion medium.
3. Preparation of Aqueous Suspended Pesticide Composition 24 parts of the above ground slurry, 40 parts of the dispersion medium, and 36 parts of water were mixed to obtain 100 parts of a homogeneous aqueous suspension of a pesticide composition.

Production Example 13

In the same manner as in Production Example 12, except that 2.3 parts of the crystal form A was changed to 1.15 parts of the crystal form A and 1.15 parts of the crystal form B, an aqueous suspension of a pesticide composition was produced.

Production Example 14

In the same manner as in Production Example 12, except that 2.3 parts of the crystal form A was changed to 2.3 parts of the crystal form B, an aqueous suspension of a pesticide composition was produced.

Test Example

Each of aqueous suspension of pesticide compositions obtained in Production Examples 12 to 14 was charged into a 30 mL volume vial bottle and was stored in a thermostatic bath of 54° C. for 14 days. The amounts of the sulfonylurea compound of Formula (1) in the compositions (hereinafter, expressed merely as "amount of the compound") before and after the storage were measured by HPLC and the decomposition rate was calculated according to the equation below. The result thereof is shown in Table 1.

Decomposition rate (%)=[(Amount of the compound before storage−Amount of the compound after storage)/(Amount of the compound before storage)]×100

TABLE 1

|  | Decomposition rate (%) |
|---|---|
| Production Example 12 | 23.4% |
| Production Example 13 | 25.4% |
| Production Example 14 | 36.8% |

INDUSTRIAL APPLICABILITY

According to the present invention, various crystals of 3-chloro-N-(4,6-dimethoxypyrimidine-2-ylcarbamoyl)-1-methyl-4-(5-methyl-5,6-dihydro-1,4,2-dioxazine-3-yl)-1H-pyrazole-5-sulfonamide can be produced. A suspension of a composition containing a specific crystal has improved storage stability, so that the composition can be used for control of weeds.

The invention claimed is:

1. A sulfonylurea compound comprising a crystal form A having peaks at 2θ=7.12°, 8.16°, 8.88°, 9.60°, 12.48°, 13.24°, 16.88°, 17.80°, 18.56°, 19.32°, 20.2°, 21.04°, 22.56°, 23.28°, 24.24°, 24.68°, 27.52°, and 31.28° in powder X-ray diffraction by a Cu—Kα ray, wherein the sulfonylurea compound is represented by the following Formula (1):

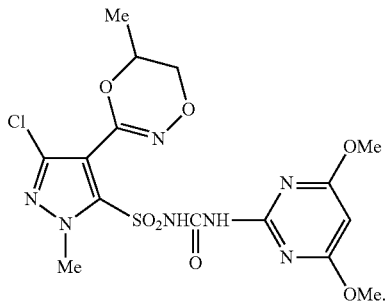

2. A suspension of a composition comprising:
the sulfonylurea compound as claimed in claim 1; and
a dispersion medium.

3. The suspension of a composition according to claim 2, further comprising:
a surfactant,
wherein the dispersion medium is water.

4. The suspension of a composition according to claim 2, wherein a content of the crystal form A in the sulfonylurea compound is 10 to 100% by weight of the sulfonylurea compound.

5. The suspension of a composition according to claim 3, wherein a content of the crystal form A in the sulfonylurea compound is 10 to 100% by weight of the sulfonylurea compound.

6. The suspension of a composition according to claim 2, wherein a content of the crystal form A in the sulfonylurea compound is 50 to 100% by weight of the sulfonylurea compound.

7. The suspension of a composition according to claim 3, wherein a content of the crystal form A in the sulfonylurea compound is 50 to 100% by weight of the sulfonylurea compound.

8. The sulfonylurea compound as claimed in claim 1, wherein the sulfonylurea compound has a melting point of 187 to 188° C.

* * * * *